United States Patent [19]

Arts et al.

[11] Patent Number: 5,702,387
[45] Date of Patent: Dec. 30, 1997

[54] COATED ELECTROSURGICAL ELECTRODE

[75] Inventors: Gene H. Arts, Berthoud; Jan E. Carr, Denver; Karen T. Kuk-Nagle, Boulder; Michael D. Lontine, Westminster, all of Colo.; Brian A. Millberg, St. Paul, Minn.

[73] Assignee: Valleylab Inc, Boulder, Colo.

[21] Appl. No.: 534,353

[22] Filed: Sep. 27, 1995

[51] Int. Cl.$^6$ .................................................. A61B 17/39
[52] U.S. Cl. ................................................. 606/45; 606/49
[58] Field of Search ........................... 606/41, 42, 45, 606/46, 49

[56] References Cited

U.S. PATENT DOCUMENTS

| | | |
|---|---|---|
| 4,087,878 | 5/1978 | Grieshaber et al. . |
| 4,314,559 | 2/1982 | Allen . |
| 4,333,467 | 6/1982 | Domicone .................. 606/45 |
| 4,492,231 | 1/1985 | Auth . |
| 4,517,975 | 5/1985 | Garito et al. ................ 606/41 |
| 4,704,760 | 11/1987 | Grieshaber . |
| 4,752,983 | 6/1988 | Grieshaber . |
| 4,785,807 | 11/1988 | Blanch . |
| 4,852,200 | 8/1989 | Phillips et al. . |
| 4,925,516 | 5/1990 | Phillips et al. . |
| 5,016,401 | 5/1991 | Mangus . |
| 5,191,670 | 3/1993 | Lake et al. . |
| 5,380,320 | 1/1995 | Morris ..................... 606/45 |
| 5,549,604 | 8/1996 | Sutco et al. ............... 606/45 |

FOREIGN PATENT DOCUMENTS

| | | |
|---|---|---|
| 637755 | 4/1992 | Australia . |
| 2594322 | 8/1987 | France ..................... 606/49 |

*Primary Examiner*—Lee S. Cohen
*Attorney, Agent, or Firm*—Peter C. Richardson; Lawrence C. Akers; Aaron Passman

[57] ABSTRACT

A design and method of manufacture is disclosed for an electrosurgical electrode with a silicone coating. The coating resists the buildup of eschar. The silicone material is thick enough in the flat area of the blade to withstand the electrosurgical voltage without breakdown. The electrosurgical current path is primarily through the blade edges and tip. The flat of the blade remains insulated under most conditions. The relatively thick coating also provides high tear strength and added durability. The composition of the electrode coatings may include silicone elastomers in the form of adhesives, dispersions, or liquid rubbers. The coating composition may also contain adhesion promoters, heat stabilizers, plasticizers, release enhancers, crosslinking agents, and colorants. Several methods of manufacture are illustrated by way of examples.

8 Claims, 1 Drawing Sheet

5,702,387

1
COATED ELECTROSURGICAL ELECTRODE

FIELD OF THE INVENTION

This invention pertains to electrosurgical electrodes which are used during surgical operations, and more particularly to a design and method of manufacture of an electrosurgical electrode with a silicone coating that resists the buildup of eschar and increases the ease of cleaning eschar build up.

BACKGROUND OF THE DISCLOSURE

Electrosurgical electrodes are used in surgical operations to cut and coagulate the tissue of a patient. The electrodes are used to conduct high frequency electrosurgical energy from a generator to the patient. Many sizes and shapes of electrosurgical electrodes are available to surgeons. Most electrosurgical electrodes are made of metal, typically stainless steel, and these electrodes typically include a fitting so that they may be inserted into a handpiece, or "pencil."

The working tip of the electrosurgical electrode is subject to high temperatures during use. This high temperature causes the proteins, carbohydrates and lipids in the body to coagulate in the tissue as well as adhere to the working tip. This coagulum is commonly called "eschar". Eschar that adheres to the working tip is undesirable because it reduces the cutting and coagulation performance of the electrosurgical electrode.

Efforts are usually made during surgery to keep the tip clean by rubbing or brushing the tip against a scouring pad. It is frequently difficult to clean the electrode. This leaves the surgeon with the options of replacing the electrode during surgery, accepting reduced performance, or expending valuable doctor's time and attention to clean the tip thoroughly.

Several methods have been used to try to solve the problem of eschar buildup. A first method is to develop better mechanisms to clean the electrode during surgery. A second method is to develop coatings for the electrosurgical electrodes to reduce eschar buildup and to make the electrode easier to clean.

Several patents disclose a method and apparatus for cleaning an electrosurgical pencil tip electrode. U.S. Pat. No. 5,016,401 has a fibrous and abrasive pad and is mounted to a hard base which could be attached to a surgical drape. U.S. Pat. No. 4,547,923 has a surgical knife cleaner with closely coiled strands supported on a base bonded by adhesive to the surgical drape. The cleaning action results when the electrode is inserted through the adjacent coils of the device; it is possibly a spring. A similar device is in U.S. Pat. No. 4,852,200.

U.S. Pat. No. 4,925,516 claims the idea of a pull off sheet to expose a tacky adhesive on the base of the knife cleaning device. There are several patents which disclose a housing having a electrode receiving slot and brushes therein for cleaning the surgical electrode. The patents are U.S. Pat. Nos. 4,752,983; 4,704,760; and 4,087,878. U.S. Pat. No. 5,191,670 shows a tubular fork cleaning apparatus having a zig-zag bristled brush therein.

Other patents have disclosed electrosurgical electrodes that are designed to resist eschar buildup. U.S. Pat. No. 4,314,559 assigned to Corning Glass Works, discloses surgical knives with bipolar electrodes thereaside to coagulate bleeding resulting from cutting with the knife edge. The '559 patent has a first conductive layer for coating the electrosurgical electrode and a second Teflon layer to provide a non-stick surface. The conductive layer is such that portions of that layer are exposed and form a connection between surgical electrode and the surface such that the Teflon only fills interstices, inclusions and the like at the surface, thus providing the non-stick surface of the cutting or coagulating instrument.

U.S. Pat. No. 4,785,807 has a primer and top coating of Teflon polymer over an etched or abraded stainless steel tip. The coating is thin and during application of electromagnetic energy it is said that there is capacitive coupling to allow passage of power to the tissue being treated.

U.S. Pat. No. 4,492,231 discusses temperature, tip conductivity and sticking of desiccated blood in a bipolar forceps.

Australian patent 637755 has a conductive shaft with insulation providing both electrical and thermal insulation and abrasion-resistance along the shaft between its ends. The insulation is provided by a shrink fitted plastic tube.

SUMMARY OF THE INVENTION

An electrosurgical electrode is disclosed which resists the buildup of eschar and improves the ease of cleaning any buildup, such as eschar, by having a coating of silicone elastomer. The silicone elastomer may be polydiorganosiloxane. The coated electrode, and the method of manufacture, are described herein.

One aspect of the design is that a relatively thick coating of silicone is used. The silicone material is thick enough in the flat area of the blade to withstand the ES (electrosurgical) voltage without breakdown. The ES path is primarily through the blade edges and tip, where the coating may be thin or non-existent. The flat of the blade remains insulated under most ES conditions. The thick coating also provides high tear strength and added durability due to cohesive bonding to itself. This makes it more durable to mechanical wear.

The composition of the electrode coatings may include silicone elastomers in the form of adhesives, dispersions, or liquid rubbers. The backbone polymer is generally but not limited to the form of $R_1R_2SiO$ where the R groups are phenyl, methyl, vinyl, or other pendant groups. In addition to the above components, the coating composition may contain some or all of the following ingredients, including adhesion promoters, heat stabilizers, fillers, plasticizers, release enhancers, crosslinking agents, and colorants.

Several processes are available for depositing the silicone elastomer. In one embodiment, the silicone elastomer is in the form of a dispersion, and the deposition is through dipping. The viscoelastic properties of the dispersions are such that when dip processed, the resultant coatings are very thin on the tip and edges of the blade and much thicker in the middle flat area. In a preferred embodiment the thin material on the edge is too thin to insulate this area from ES current and, when ES energy is keyed, immediately conducts current. With the edges conducting and the flat area insulated, the ability to cut is enhanced by creating a high current density on the edge which rapidly generates a steam barrier for cutting. The dip process also creates a thick coating on the flat area with a radius profile which can enhance cleanability because when the blade is wiped against a surface, the radius provides a high point of contact and thus higher pressure on the flat of the blade, higher in the center and diminishing toward the edge.

The silicone coated blade is cleanable and non-stick because the silicone does not wet out, which provides a very poor bonding surface for the eschar. Further, the elastomeric surface yields to mechanical action (wiping or cutting). This breaks the bond to the eschar. Additionally, the tissue in contact with the silicone surface does not reach the temperatures required for significant eschar sticking because the silicone surface is thermally insulated and there is relatively little ES current conduction in that area. This represents a significant area of the blade.

The disclosed silicone coated blade has advantages over presently available ES blades. It provides better cutting (more consistent from the very beginning and requiring lower power) because the edges of the blade are conductive to ES whereas the flat is not significantly conductive. This may allow a steam barrier, which is desirable for cutting, to be generated more rapidly. There is also more consistent cleaning performance because the flat of the blade, which represents the greatest amount of surface area, remains substantially insulated (no pin holes or deterioration) during extended use. The radius profile which extends from the flat area of the blade will enhance cleanability. A surgeon may also apply ES energy to hemostats with the edge of the blade without damage to the coating. The coated blade is also bendable without significant damage to the coating.

Silicone adhesives may be a one component, self leveling silicone elastomer containing no solvents. One example is NuSil Med-1511, supplied by NuSil Technology, Inc. located in Carpinteria, Calif. It may be diluted in an organic solvent to 30%–70% solids, preferably being 50% solids. The acetoxy curing mechanism of this system occurs at room temperature and in the range of 20%–60% relative humidity. During the curing process, the silicone adhesive releases acetic acid vapor as a by-product.

Silicone dispersion may be a two component system of medium viscosity liquids that are blended at a 1:1 ratio by weight or volume. One example is NuSil Med-6640. It may be 25% solids dispersed in an organic solvent and may be further diluted to 7% solids. The dispersion can be made from a high consistency silicone gum with 5000 degrees of polymerization on the average. The platinum addition cure mechanism of this system occurs at elevated temperatures.

Liquid silicone rubbers may be a two component system containing 100% silicone elastomer paste that are blended at a 1:1 ratio. One example is Applied SiLSR-50, supplied by Applied Silicone Corporation, located in Ventura, Calif. Disproportionation of these components can enhance adhesion to the substrate. The elastomer may be diluted in an organic solvent to 20%–50% solids, preferably being 30% solids. The platinum addition cure mechanism of this system occurs at elevated temperatures. The durometer or hardness of the LSR can be in the range of 5–70, but is preferably 50.

A silicone coated blade may be manufactured as follows. A steel electrosurgical electrode may have its outer surfaces roughened in order to improve the adhesion of a primer. In the preferred embodiment, the uncoated electrode is sandblasted so that it has a surface roughness in the range of 50 to 250μin Ra but preferably 175 to 225 or greater. The sandblasting process may be accomplished with 16 to 100 grit aluminum oxide, although other roughening techniques may also be used.

A primer is applied to the roughened electrode. The primer is a polysiloxane resin. It may be a mixture of two tetrafunctional silanes, a tetrafunctional titanate, and an appropriate crosslinking catalyst. The thickness of the primer is typically less than 100Å.

The primed electrode is coated with silicone elastomer polymer. Several types of silicone polymers are effective. The preferred embodiment uses methylvinyl polydimethylsiloxane with vinyl endblock functionality. The total thickness of the silicone coating is nominally 3 to 20 mils. The uniformity of the thickness is most preferably adjusted thinner in certain areas to provide less dielectric strength where passage of high frequency electromagnetic energy is preferred for cutting. The uniformity of the thickness is most preferably adjusted thicker in other certain areas to provide more dielectric strength where no passage of high frequency electromagnetic energy is preferred to enhance non-stick and ease of cleaning properties.

Several methods of curing the silicone elastomers are available. The preferred method for curing is an addition reaction using organoplatinum compound catalysis and heat. Other curing methods include condensation reactions, utilizing ambient moisture, UV initiated moisture cure, and peroxide vulcanization.

DETAILED DESCRIPTION OF THE INVENTION

Figure 1:
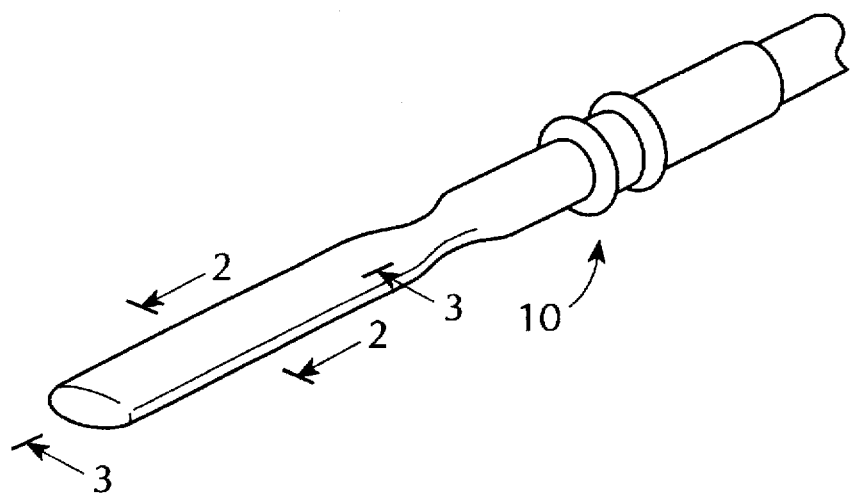
FIG. 1 is a perspective view of the non-uniformly coated electrode having a blade shape.
Figure 2:
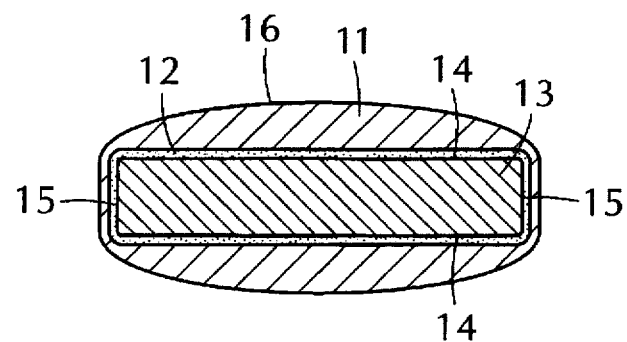
FIG. 2 is a view in cross section taken along line 2—2 of FIG. 1 and showing the conductive metallic electrode with a primer coating and a silicone top-coating; the primer and silicone are shown enlarged for purposes of illustration.
Figure 3:
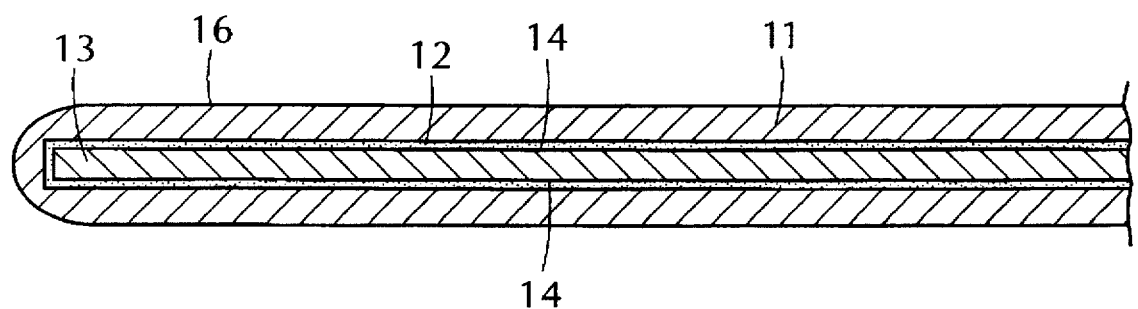
FIG. 3 is a longitudinal view in cross section of the electrode of FIG. 1 as seen from the plane of lines 3—3 thereof and showing the metallic conductive electrode with the primer and silicone enlarged and not to scale for illustrative purposes.

A coated electrosurgical electrode 10, as shown in FIG. 1, resists the buildup of eschar and improves the ease of cleaning any build up, such as eschar. The electrode 10 has a coating of silicone elastomer 11, as shown in FIGS. 2 and 3, preferably comprising polydiorganosiloxane. The coated electrode 10, and its methods of manufacture are described herein. Several alternative manufacturing techniques are disclosed by way of examples.

In one embodiment, a medical grade stainless steel electrosurgical electrode 13 may have its outer surfaces roughened in order to improve the adhesion of a primer 12. The uncoated electrode is sandblasted so that it has a surface roughness in the range of 50 to 250 μin Ra but preferably 175 to 225. The sandblasting process may be accomplished with 16 to 100 grit aluminum oxide, although other roughening techniques may also be used. The roughening pretreatment to enhance adhesion can include media blasting, tumbling, stamped texture, perforations through the metallic conductive substrate by for example EDM, chemical etching or eroding with acid or caustic.

A primer 12 is applied to the roughened electrode metallic conductive substrate 13. The primer 12 is preferably a polysiloxane resin. The thickness of the primer 12 is typically less than 100 Å and the primer 12 is uniformly applied.

The primed electrode is overcoated with silicone elastomer polymer 11. Several types of silicone polymers are effective. One embodiment has a methylvinyl polydimethylsiloxane with vinyl endblock functionality and filler, preferably an amorphous silica filler. The total thickness of the silicone coating is nominally 3 to 20 mils.

The thickness of the silicone coating 11 is non-uniform. The silicone coating 11 is preferably thinner where passage of high frequency electrical current is desirable for cutting, for example along the edges of the electrosurgical blade and at the tip, as shown in FIGS. 2 and 3. The thickness of the silicone coating 11 is preferably greater in other areas in order to enhance cleanability, for example on the major surfaces of the blade, as shown in FIG. 2. A non-uniform coating is also meant to describe the configuration where the major surfaces 14 have a silicone coating while the edges 15 are not coated. The term "thickness" is meant to describe the dimension between the substrate 13 and one outer surface 16 of the coating.

The significance of a non-uniform coating 12 is that high frequency electrical current will be conducted preferentially through regions of the electrode 10 where the electrical resistance is low. If the coating on the edges 15 of the electrode 10 is thin, or non-existent, then current will be conducted preferentially through the edges 15. The flat, or major surfaces 14, may have a thicker coating which will provide greater electrical insulation than occurs at the edges 15. This can result in an increased cutting efficiency and a lower tendency for buildup of eschar on the major surfaces 14.

It has been found through experimentation that ionizing irradiation of up to 10 megarads has a beneficial effect on the silicone coating. In particular, the irradiated silicone coating showed improved adhesion and reduced tackiness.

Several additional examples of methods of manufacturing a coated electrosurgical blade follow. Example numbers 4, 5, and 6 are preferred variations of the same basic manufacturing process. Example number 9 is also a preferred embodiment.

EXAMPLE 1

304 series stainless steel electrode blades sandblasted with 80 grit aluminum oxide media to a surface roughness of 50–80 μin Ra were ultrasonically cleaned in an acetone bath for 15 minutes and were then primed with SP-120. The primer was allowed to air dry for 1 hour at ambient conditions. The blades were then dip-coated in a solution of NuvaSil 5083, a UV/moisture cure adhesive supplied by Loctite Corporation located in Hartford, Conn. The solution was dissolved to 14% by weight solids in xylene. The blades were allowed to flash at ambient conditions for 30 minutes and then placed under a UV light providing 400 mW/cm$^2$ of UV energy at a wavelength of 365 nm for 30 seconds on each side of the blade. The coated blades were then allowed to air cure at ambient conditions for 48 hours.

EXAMPLE 2

Electrode blades were sandblasted with 80 grit aluminum oxide media to a surface roughness of 50–80 μin Ra. They then were ultrasonically cleaned in an acetone bath for 15 minutes. The blades were then primed with NuSil CF6-135, supplied by NuSil Technology, Inc. The primer was allowed to air dry for 30 minutes at ambient conditions. The blades were then dip-coated in a solution consisting of 44% NuSil MED-6640 silicone elastomer dispersion and 56% xylene by weight. The resulting mixed solution concentration of elastomer solids was 11%. Two types of coated blades were obtained from this solution, one type was dipped only once while the other type was allowed to flash for 20 minutes at ambient conditions and then was dipped again into the solution. Both types were allowed to flash for a minimum of 20 minutes after their last dip, and then cured in a forced air convection oven at 75°±2° C. for 45 minutes, followed by 135 minutes in a forced air convection oven at 150°±5° C. This process yielded blades with a film thickness of 0.8 to 1.5 mils.

EXAMPLE 3

Electrosurgery blades prepared as in Example 2 above were coated with the same 11% weight solids solution of Nusil MED-6640 in xylene. The method of coating application was electrostatic spray, with the blade as the grounded portion of the circuit. After 1–3 passes of the spray nozzle, the coated blades were allowed to flash at ambient conditions for 30 minutes prior to curing in the same manner as the blades in Example 2. The film thickness was in the range of 1.0 to 2.5 mils.

EXAMPLE 4

The blades and Nusil MED-6640 of Example 2 were used in a multiple dip process to produce thicker films on the finished product. The solution weight solids were reduced to 9% with the addition of more xylene. This change was made to improve the uniformity of the coating along the length of the blade. The blades were dipped perpendicular to the solution surface, immersed in the solution to a depth that fully covered the flat portion of the blade, removed at the same angle of entry, flipped 180° and held for 10 seconds, and then rotated in a complex helical pattern to assure even film thickness along the blade length. After 20 minutes of rotation, the dipping process was repeated up to a total of 8 dips. After the last 20 minute rotation, the blades were placed into a forced air convection oven and cured for 135 minutes at 160° C. On each individual blade, the film thickness ranged from 3 mils to 6 mils, with the heaviest coating at the blade tip.

EXAMPLE 5

Two individual sets of electrode blades sandblasted with 80 grit aluminum oxide media to surface roughness of 50 to 120 μin Ra. The blades then were ultrasonically cleaned in an acetone bath for 15 minutes. The blades were then primed with CF6-135. The primer was allowed to air dry for 30 minutes at ambient conditions. The blades were then dip-coated in a solution of MED-6640 diluted to 9% weight solids in xylene. The blades were dipped perpendicular to the solution surface, immersed in the solution to a depth that fully covered the flat portion of the blade, removed at the same angle of entry, flipped 180° and held for 6 seconds, and then rotated in a complex helical pattern to assure even film thickness along the blade length. After 20 minutes of rotation, the dipping process was repeated up to a total of 6 or 10 dips. After the last 20 minute rotation, the blades were placed into a forced air convection oven and cured for 135 minutes at 160° C. On each individual blade, the film thickness ranged from 3.5 mils for the blades dipped 6 times to 6 mils for the blades dipped 10 times.

EXAMPLE 6

Electrode blades were sandblasted with 80 grit aluminum oxide media to surface roughness of 120 μin Ra. The blades then were ultrasonically cleaned in an acetone bath for 15 minutes. The blades were then primed with CF6-135. The primer was allowed to air dry for 30 minutes at ambient conditions. The blades were then dip-coated in a solution of MED-6640 diluted to 9% weight solids in xylene. The blades were dipped perpendicular to the solution surface, immersed in the solution to a depth that fully covered the flat portion of the blade, removed at the same angle of entry, flipped 180° and held for 6 seconds, and then rotated in a complex helical pattern to assure even film thickness along the blade length. After 20 minutes of rotation, the dipping process was repeated up to a total of 13 dips. After the last 20 minute rotation, the blades were placed into a forced air convection oven and cured for 135 minutes at 160° C. On each individual blade, the film thickness ranged from 5 to 8 mils.

EXAMPLE 7

Electrode blades were sandblasted with aluminum oxide media to achieve a surface roughness of 120 Ra. The blades then were ultrasonically cleaned in an acetone bath for 15 minutes. Holes ranging in diameter from 0.005 in. to 0.075 in. were drilled through the flat portion of the blade to provide a location for silicone elastomer to encapsulate the blade with enhanced adhesion. The blades were then placed into a compression/transfer mold and NuSil MED-4750 was forced into the cavity, coating the two blade faces and penetrating the blade surface via the drilled holes. After 10 minutes in the mold at 240 deg. F., the mold was opened and the coated blade removed. On each individual blade, the film thickness ranged from 2 to 4 mils.

EXAMPLE 8

Blades were prepared in the same manner as Example 7, with the elastomer used for the molding being NuSil MED-4720 in place of the NuSil MED-4750.

EXAMPLE 9

Blades were prepared in the same manner and dip coated in the same manner as Example 6. Before curing the silicone elastomer, a Teflon spray release was applied to the surface of the coated blades just prior to placing the blades into the curing oven. The spray release was Tiolon X-20, supplied by Tiodize Co. of Huntington Beach, Calif., which is a mixture of polytetrafluoroethylene particles dispersed in organic solvent and a propellant for aerosol spray. The blades were then cured as in Example 6.

EXAMPLE 10

Electrode blades were sandblasted with alumina oxide media to a surface roughness of 50–250 Ra, preferably 200 Ra. Next, the blades were ultrasonically cleaned in an acetone bath for 15 minutes. The blades were then primed with NuSil SP-120 by dipping the blades into the primer and allowing them to air dry at ambient conditions for 30 minutes. The blades were then dip coated in a solution of NuSil Technology MED-1511 silicone adhesive, 30%–70% solids in toluene. The silicone adhesive solution was maintained under nitrogen to prevent curing of the silicone due to moisture contact. The primed blades were dipped into the silicone solution and allowed to solvent flash and set up for 1 hour. The blades were then dipped once again, and allowed to crosslink fully via an acetoxy cure mechanism for 24 hours at ambient conditions. The resultant coating thickness at the tip of the electrode was 8 mils.

EXAMPLE 11

Electrode blades, sandblasted with alumina oxide media to a surface roughness of 50–250 Ra (preferably 200 Ra), were ultrasonically cleaned in an acetone bath for 15 minutes. The blades were then primed with Applied Silicone medical grade primer for metals and plastics by dipping the blades into the primer and allowing them to air dry at ambient conditions for 30 minutes. The blades were then dip coated in a solution of Applied Silicone two part liquid silicone rubber (1:1 ratio, 50 durometer), at 20%–50% solids (preferably 33%) in naphtha, and allowed to flash in a room temperature convection air oven for 10 minutes. This dipping procedure was repeated four more times to produce a coating thickness of 10 mils at the tip of the electrode. The coating was then cured for 1 hour at 165 degrees C.

EXAMPLE 12

Coated electrodes similar to example 7 were subjected to ion treatment in order to further the crosslinking and reduce the tackiness of the silicone surface. Blades were subjected to RF excited argon plasma in a vacuum for 7 minutes.

EXAMPLE 13

Coated electrodes, similar to Example 7 were subjected to ion treatment in order to further the crosslinking and reduce the tackiness of the silicone surface. Blades were subjected to electron beam irradiation doses of 2.5, 5.0, and 10.0 megarads.

What is claimed is:

1. An electrode for an electrosurgical tool to be used for surgery on the tissue of a patient, the electrode comprising:
   an elongate metallic shaft having a proximal end and a distal end, wherein the proximal end is shaped for insertion into the electrosurgical tool for conducting electrosurgical energy;
   a patient end portion at the distal end for manipulation of the tissue of the patient;
   a top coating on the patient end portion, the top coating comprising a polydiorganosiloxane elastomer, wherein the top coating is of non-uniform thickness over the patient end portion.

2. The electrode of claim 1 further comprising a base coating of primer material underneath the top coating, the base coating comprising a polysiloxane resin with a crosslinking catalyst.

3. The electrode of claim 1 wherein the distal end is blade-like in shape, having at least two major surfaces which are generally parallel and are bounded by an edge.

4. The electrode of claim 3 wherein the non-uniform thickness provides lesser electrical conductivity over the major surfaces than along the edge.

5. The electrode of claim 3 wherein the major surfaces are coated to achieve a higher dielectric value than the bounding edge.

6. The electrode of claim 5 wherein the higher dielectric value results from a generally thicker top coating across primarily the major surfaces.

7. The electrode of claim 1 wherein the patient end portion, before being coated, has a surface roughness in the range of about 50 to 250 µin Ra.

8. An electrode for an electrosurgical tool to be used for surgery on the tissue of a patient, the electrode comprising:
   an elongate metallic shaft having a proximal end and a distal end, wherein the proximal end is shaped for insertion into the electrosurgical tool for conducting electrosurgical energy, wherein the distal end is blade-like in shape with at least two major surfaces which are generally parallel and are bounded by an edge;
   a patient end portion at the distal end for manipulation of the tissue of the patient, wherein the patient end portion, before being coated, has a surface roughness in the range of about 50 to 250µ0 in Ra;
   a base coating of primer material on the patient end portion, the base coating comprising a polysiloxane resin with a crosslinking catalyst;

a top coating over the base coating, the top coating comprising a polydiorganosiloxane elastomer, wherein the top coating is of non-uniform thickness over the patient end portion, wherein the major surfaces are coated to achieve a higher dielectric value than the bounding edge.

* * * * *